US008870914B2

(12) United States Patent
Hoffman et al.

(10) Patent No.: US 8,870,914 B2
(45) Date of Patent: Oct. 28, 2014

(54) MEDICAL DEVICE AND A METHOD FOR SEALING A PUNCTURE OR AN OPENING

(75) Inventors: Grant T. Hoffman, Bloomington, IN (US); James B. Hunt, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1206 days.

(21) Appl. No.: 11/900,231

(22) Filed: Sep. 11, 2007

(65) Prior Publication Data

US 2008/0071310 A1 Mar. 20, 2008

Related U.S. Application Data

(60) Provisional application No. 60/844,149, filed on Sep. 12, 2006.

(51) Int. Cl.
*A61B 17/08* (2006.01)
*A61B 17/00* (2006.01)

(52) U.S. Cl.
CPC ... *A61B 17/0057* (2013.01); *A61B 2017/00659* (2013.01); *A61B 2017/00637* (2013.01); *A61B 17/00491* (2013.01); *A61B 2017/00889* (2013.01)
USPC .......................................... 606/213; 606/215

(58) Field of Classification Search
CPC .................. A61B 17/0057; A61B 2017/00637
USPC ........................... 606/213, 139, 151, 215, 232
See application file for complete search history.

(56) References Cited

U.S. PATENT DOCUMENTS

| 3,225,766 | A | * | 12/1965 | Baptist et al. ................. 606/230 |
|---|---|---|---|---|
| 4,762,129 | A | | 8/1988 | Bonzel |
| 4,852,568 | A | | 8/1989 | Kensey |
| 4,890,612 | A | | 1/1990 | Kensey |
| 4,902,508 | A | | 2/1990 | Badylak et al. |
| 5,342,393 | A | | 8/1994 | Stack |
| 5,350,399 | A | | 9/1994 | Erlebacher et al. |
| 5,370,660 | A | | 12/1994 | Weinstein et al. |

(Continued)

FOREIGN PATENT DOCUMENTS

WO WO 98/22158 8/1997

OTHER PUBLICATIONS

Heeschen, C., et al., "Nicotine stimulates angiogenesis and promotes tumor growth and atherosclerosis," *Nature Medicine*, 7(7):833-839 (2001).

(Continued)

*Primary Examiner* — Gregory Anderson
(74) *Attorney, Agent, or Firm* — Brinks Gilson & Lione

(57) ABSTRACT

The invention is generally directed to devices and methods for sealing a puncture or an opening through a wall of a blood vessel or a body cavity. The device includes a structural member and a sealing material associated with the structural member. The structural member includes a rod, a first obstructing body and a second obstructing body. The first obstructing body is affixed against an inner surface of the wall of the blood vessel or body cavity and the second obstructing body is affixed against an outer surface of the wall of the blood vessel or body cavity once placed at the puncture or the opening. The sealing material includes a reconstituted or naturally-derived collagenous material, which can expand at the puncture or the opening to restore hemostasis and enhance sealing.

42 Claims, 14 Drawing Sheets

(56) References Cited

U.S. PATENT DOCUMENTS

| | | | |
|---|---|---|---|
| 5,411,520 A | | 5/1995 | Nash et al. |
| 5,531,759 A | * | 7/1996 | Kensey et al. ............... 606/213 |
| 5,690,643 A | | 11/1997 | Wijay |
| 5,725,552 A | | 3/1998 | Kotula et al. |
| 5,733,337 A | | 3/1998 | Carr, Jr. et al. |
| 5,814,061 A | | 9/1998 | Osborne et al. |
| 5,853,422 A | * | 12/1998 | Huebsch et al. ............. 606/213 |
| 6,123,715 A | | 9/2000 | Amplatz |
| 6,174,322 B1 | * | 1/2001 | Schneidt ..................... 606/213 |
| 6,206,931 B1 | | 3/2001 | Cook et al. |
| 6,371,961 B1 | | 4/2002 | Osborne et al. |
| 2002/0077656 A1 | | 6/2002 | Ginn et al. |
| 2003/0171772 A1 | | 9/2003 | Amplatz |
| 2004/0180042 A1 | | 9/2004 | Cook et al. |
| 2007/0118176 A1 | * | 5/2007 | Opolski et al. ............... 606/213 |
| 2010/0030259 A1 | | 2/2010 | Pavcnik et al. |

OTHER PUBLICATIONS

Huynh, T., et al., "Remodeling of an acellular collagen graft into a physiologically responsive neovessel," *Nature Biotechnology*, 17:1083-1086 (1999).

Johnson, C., et al., "Matrix Metalloproteinase-9 Is Required for Adequate Angiogenic Revascularization of Ischemic Tissues, Potential Role in Capillary Branching," *Circulation Research*, 94:262-268 (2004).

Lee, K.Y., et al., "Controlling Mechanical and Swelling Properties of Alginate Hydrogels Independently by Cross-Linker Type and Cross-Linking Density," *Macromolecules*, 33:4291-4294 (2000).

Poirier, Y. et al., "Production of Polyhydroxyalkanoates, a Family of Biodegradable Plastics and Elastomers, in Bacteria and Plants," *Bio/Technology*, 13:142-150 (1995).

Sodian, R., et al., "Fabrication of a Trileaflet Heart Valve Scaffold from a Polyhydroxyalkanoate Biopolyester for Use in Tissue Engineering," *Tissue Engineering*, 6(2):183-189 (2000).

Temenoff, J.S., et al., "Effect of Poly(ethylene glycol) Molecular Weight on Tensile and Swelling Properties of Oligo(poly(ethylene glycol)fumarate) Hydrogels for Cartilage Tissue Engineering," *J. Biomed. Mater. Res.*, 59:429-437 (2002).

Urry, D.W., et al., "Elastic Protein-based Polymers in Soft Tissue Augmentation and Generation," *J. Biomater. Sci, Polym. Ed.*, 9(10):1015-1048 (1998).

van Hest, J.C.M. & Tirrell, D.A., "Protein-based Materials, Toward a New Level of Structural Control," *Chem. Comm.*, 19:1897-1904 (2001).

Wang, Y., et al., "A Tough Biodegradable Elastomer," *Nature Biotechnology*, 20:602-606 (Jun. 2002).

Welsh, E.R. & Tirrell, D.A., "Engineering the Extracellular Matrix: A Novel Approach to Polymeric Biomaterials. I. Control of the Physical Properties of Artificial Protein Matrices Designed to Support Adhesion of Vascular Endothelial Cells," *Biomacromolecules*, 1:23-30 (2000).

U.S. Appl. No. 13/111,338, filed May 19, 2011, Paul, Jr.

* cited by examiner

MEDICAL DEVICE AND A METHOD FOR SEALING A PUNCTURE OR AN OPENING

RELATED APPLICATIONS

The present patent document claims the benefit of the filing date under 35 U.S.C. §119(e) of Provisional U.S. Patent Application Ser. No. 60/844,149, filed Sep. 12, 2006, which is hereby incorporated by reference.

BACKGROUND OF INVENTION

1. Technical Field

This invention relates to medical devices and methods that facilitate sealing and closure of punctures and openings in or between tissue structures, the wall of a blood vessel or the wall of a body cavity.

2. Background Information

The control of bleeding during and after surgery is important to the success of the procedure. The control of blood loss is of particular concern if the surgical procedure is performed directly upon or involves the patient's arteries and veins.

Typically, the insertion of a catheter creates a puncture through the vessel wall and upon removal the catheter leaves a puncture opening through which blood may escape and leak into the surrounding tissues. Therefore, unless the puncture site is closed, clinical complications may result leading to increased hospital stays with the associated costs. To address this concern, medical personnel are required to provide constant and continuing care to a patient who has undergone a procedure involving an arterial or venous puncture to ensure that post-operative bleeding is controlled.

A common method of healing the puncture to the vessel is to maintain external pressure over the vessel until the puncture seals by natural clot formation processes. This method of puncture closure typically takes about thirty to ninety minutes, with the length of time usually being greater if the patient is hypertensive or anti-coagulated.

Furthermore, it should be appreciated that utilizing pressure, such as human hand pressure, to control bleeding suffers from several drawbacks regardless of whether the patient is hypertensive or anti-coagulated. In particular, human hand pressure can be uncomfortable for the patient, can result in excessive restriction or interruption of blood flow, and can use costly professional time on the part of the hospital staff. Other pressure techniques, such as pressure bandages, sandbags, or clamps require the patient to remain motionless for an extended period of time and the patient must be closely monitored to ensure the effectiveness of these techniques.

Devices have been disclosed which plug or otherwise provide an obstruction in the area of the puncture (see, for example, U.S. Pat. Nos. 4,852,568 and 4,890,612) wherein a collagen plug is disposed in the blood vessel opening. When the plug is exposed to body fluids, it swells to block the wound in the vessel wall. Other plug-like devices are disclosed, for example, in U.S. Pat. Nos. 5,342,393; 5,370,660; and 5,411,520; and U.S. Publication No. 2002/0077656 A1.

Yet another example of a device for sealing punctures was previously described in U.S. patent application Ser. No. 11/396,377. Specifically, the device included a closure member, such as a collapsible basket, ECM material and a hemostatic material.

Accordingly, medical devices and methods for closing wounds in the vasculature or in the wall of a body cavity, such as a heart chamber, or a body cavity of another organ of a patient are extremely beneficial. Devices having the ability to consistently, reliably, and quickly close the puncture wound eliminate the prolonged bleeding currently associated with such wounds, prevent disposing any occlusive material into the vessel or body cavity, and prevent introducing infectious organisms into the patient's circulatory system.

SUMMARY OF INVENTION

In one embodiment, the invention is a medical device for sealing a puncture or an opening through a wall of a blood vessel or a body cavity. The device includes a structural member which can be in a first collapsed configuration and in a second expanded configuration and a sealing material associated with the structural member comprising a reconstituted or naturally-derived collagenous material, wherein the collagenous material expands at the puncture or the opening. The structural member includes a rod comprising a biodegradable polymer and having a distal end and a proximal end, a first obstructing body disposed on the distal end of the rod, and a second obstructing body disposed on the proximal end of the rod. The first and the second obstructing bodies are opposing each other once the structural member is in the expanded configuration. The first obstructing body is affixed against an inner surface of the wall of the blood vessel or body cavity and the second obstructing body is affixed against an outer surface of the wall of the blood vessel or body cavity once the structural member is placed at the puncture or the opening.

The first obstructing body and the second obstructing body may include prongs. The first obstructing body may be a plug, an expandable and collapsible basket, a disc, prongs, a circular frame, or an oval frame. The second obstructing body may be a plug, an expandable and collapsible basket, a disc, prongs, a circular frame, or an oval frame.

In one embodiment, at least a portion of the rod comprises structural elements for adjusting the distance between the first and the second obstructing bodies.

In certain embodiments, the medical device further includes a delivery member, such as a catheter.

In one embodiment, the medical device is for sealing a vascular puncture made during a vascular, endoscopic, or orthopaedic surgical procedures. Alternative, the device is for sealing a septum.

In another embodiment, the invention is a method for sealing a puncture or an opening through a wall of a blood vessel or a body cavity. The method includes providing a device comprising a structural member comprising a rod comprising a biodegradable polymer and having a distal end and a proximal end, a first obstructing body disposed on the distal end of the rod; and a second obstructing body disposed on the proximal end of the rod; and a sealing material associated with the structural member comprising reconstituted or naturally derived collagenous material, the device being in a first compacted configuration. The method further includes deploying though a delivery member at site of puncture or opening the distal end of the rod on a luminal side of the blood vessel or body cavity so that the first obstructing body engages the inner surface of the wall of the blood vessel or body cavity at the puncture or the opening. The method also includes deploying through a delivery member at site of puncture or the opening the proximal end of the rod on an outer side of the blood vessel or body cavity so that the second obstructing body is positioned on an outer surface of the wall of the blood vessel or body cavity at the puncture or the opening. The first obstructing body and the second obstructing body radially expand so that the structural member assumes a second expanded configuration following the deployment at the puncture or the opening and the collagenous material expands upon contact with tissue at the puncture or the opening. Preferably, the second obstructing body is disposed on the proximal end of the rod after the proximal end of the rod is deployed. Preferably, the method further includes adjusting the distance between the first and the second obstructing bodies.

DETAILED DESCRIPTION OF THE DRAWINGS AND THE PRESENTLY PREFERRED EMBODIMENTS

The present medical devices and methods are especially useful for sealing vascular and other punctures or openings by delivering the device to that area.

Specifically, the medical devices and methods of the present invention can be used to seal a puncture or an opening in a tubular tissue structure, such as a blood vessel, or in the wall of a body cavity, that has been created intentionally or unintentionally during a surgical procedure, such as punctures which have been created during diagnostic and interventional vascular and peripheral catheterizations, or nonsurgically (e.g., during an accident). Punctures made intentionally include vascular punctures made in various types of vascular, endoscopic, or orthopaedic surgical procedures, or punctures made in any other type of surgical procedure, in coronary and in peripheral arteries and veins or in the wall of a body cavity. Such procedures include angiographic examination, angioplasty, laser angioplasty, valvuloplasty, atherectomy, stent deployment, rotablator treatment, aortic prosthesis implantation, intraortic balloon pump treatment, pacemaker implantation, any intracardiac procedure, electrophysiological procedures, interventional radiology, and various other diagnostic, prophylactic, and therapeutic procedures such as dialysis and procedures relating to percutaneous extracorporeal circulation.

The medical devices and methods of the present invention can also be used to seal an opening between tissue structures, such as a septum, including a heart septum, nasal septum, and general holes in tissue.

Other uses for the present devices and methods are also contemplated.

Figure 1:
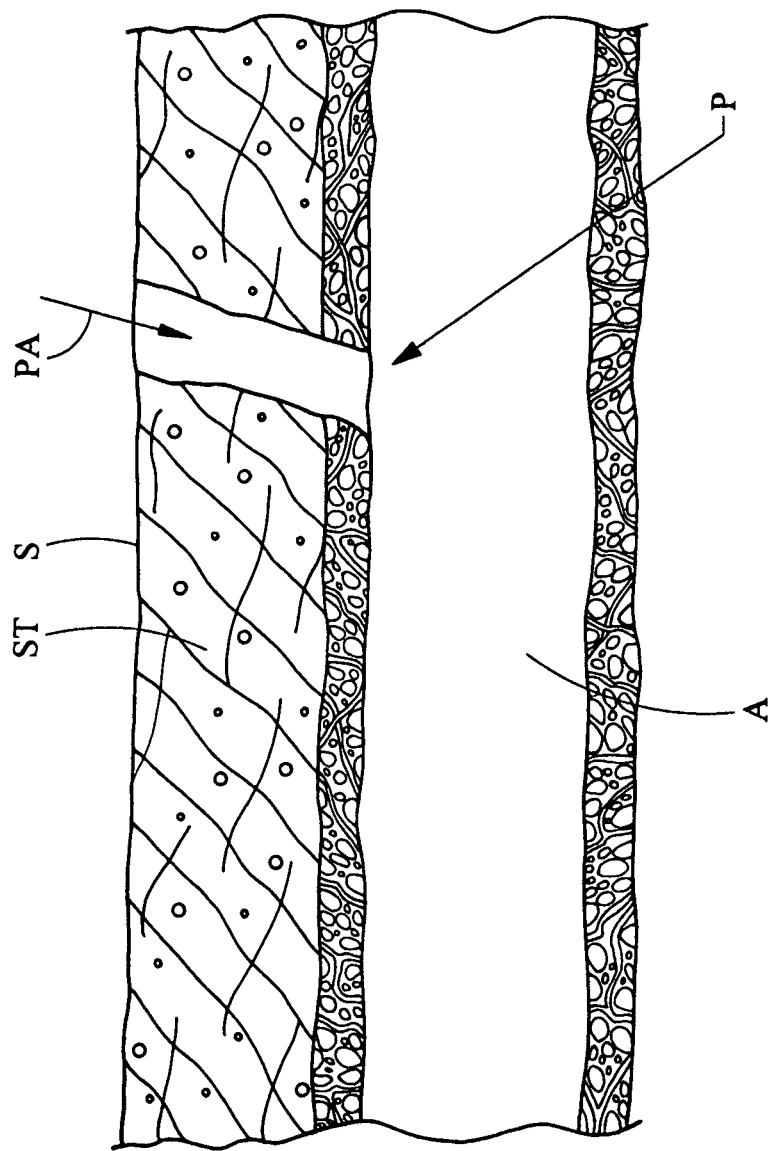
FIG. 1 is a schematic illustration of a punctured tubular tissue structure, such as an artery.

Referring to FIG. 1, patient's artery A is shown in cross section passing beneath the skin S and subcutaneous tissue ST. The artery has been accessed by way of a percutaneous surgical procedure, which has resulted in an arterial access site passing through puncture P in the wall of the artery A. For example, puncture P in the wall of the artery A may have resulted from inserting a catheter along path PA, though puncture P, and into the interior of artery A.

To seal such or similar puncture or an opening in tissue, the devices and methods of the present invention employ a structural member and a sealing material. Upon the placement of the device at the puncture, the structural member closes the puncture and provides a structural support by maintaining its shape at the puncture, and the sealing material restores hemostasis and promotes the tissue ingrowth at the puncture to further enhance the sealing provided by the structural member at the puncture. Furthermore, the presence of the structural member allows the medical device to be used to seal larger puncture channels or openings, such as 9-16 Fr, which typically fall outside the capabilities of, for example, collagen foam plugs known in the art. This is due primarily to the fact that the structural member of this invention generally maintains its structure for a long period of time (days, weeks, months).

In the discussion herein, a number of terms are used. In order to provide a clear and consistent understanding of the specification and claims, the following definitions are provided.

"Biocompatibility" refers to the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests assay as to a material's toxicity, infectivity, pyrogenicity, irritation potential, reactivity, hemolytic activity, carcinogenicity, and/or immunogenicity. A biocompatible structure or material when introduced into a majority of patients will not cause an adverse reaction or response. In addition, it is contemplated that biocompatibility can be effected by other contaminants such as prions, surfactants, oligonucleotides, and other biocompatibility effecting agents or contaminants. Biocompatible material includes biodegradable materials.

The term "biodegradable" refers to ability of a material to disintegrate or degrade so that no material remains after a specified period of time.

"Contaminant" refers to an unwanted substance on, attached to, or within a material. This includes, but is not limited to: bioburden, endotoxins, processing agents such as antimicrobial agents, blood, blood components, viruses, DNA, RNA, spores, fragments of unwanted tissue layers, cellular debris, and mucosa.

"Catheter" refers to a tube that is inserted into a blood vessel to access the vessel. Catheter includes catheter per se, introducer sheath and other suitable medical devices.

The term "proximal" refers to an area nearer to a point of reference such as an origin or a point of attachment. In this application the term proximal refers to an area nearer to a physician.

The term "distal" refers to an area further from a point of reference such as an origin or a point of attachment. In this application the term distal refers to an area furthest from a physician.

The term "inner surface" refers to a luminal surface of a wall of a blood vessel or a wall of a body cavity.

The term "outer surface" refers to an outer surface (exluminal surface) of a wall of a blood vessel or a wall of a body cavity.

When the opening is a septum between two body cavities, the "outer surface" is the surface proximal to a physician, and the "inner surface" is the surface distal to the physician.

Medical Device

The invention is a medical device for sealing a puncture or an opening through a tissue structure, including a wall of a blood vessel or a wall of a body cavity, comprising a structural member and a sealing material. The structural member and the sealing material are further described in the non-limiting disclosure set forth below.

1. Structural Member

Figure 2:
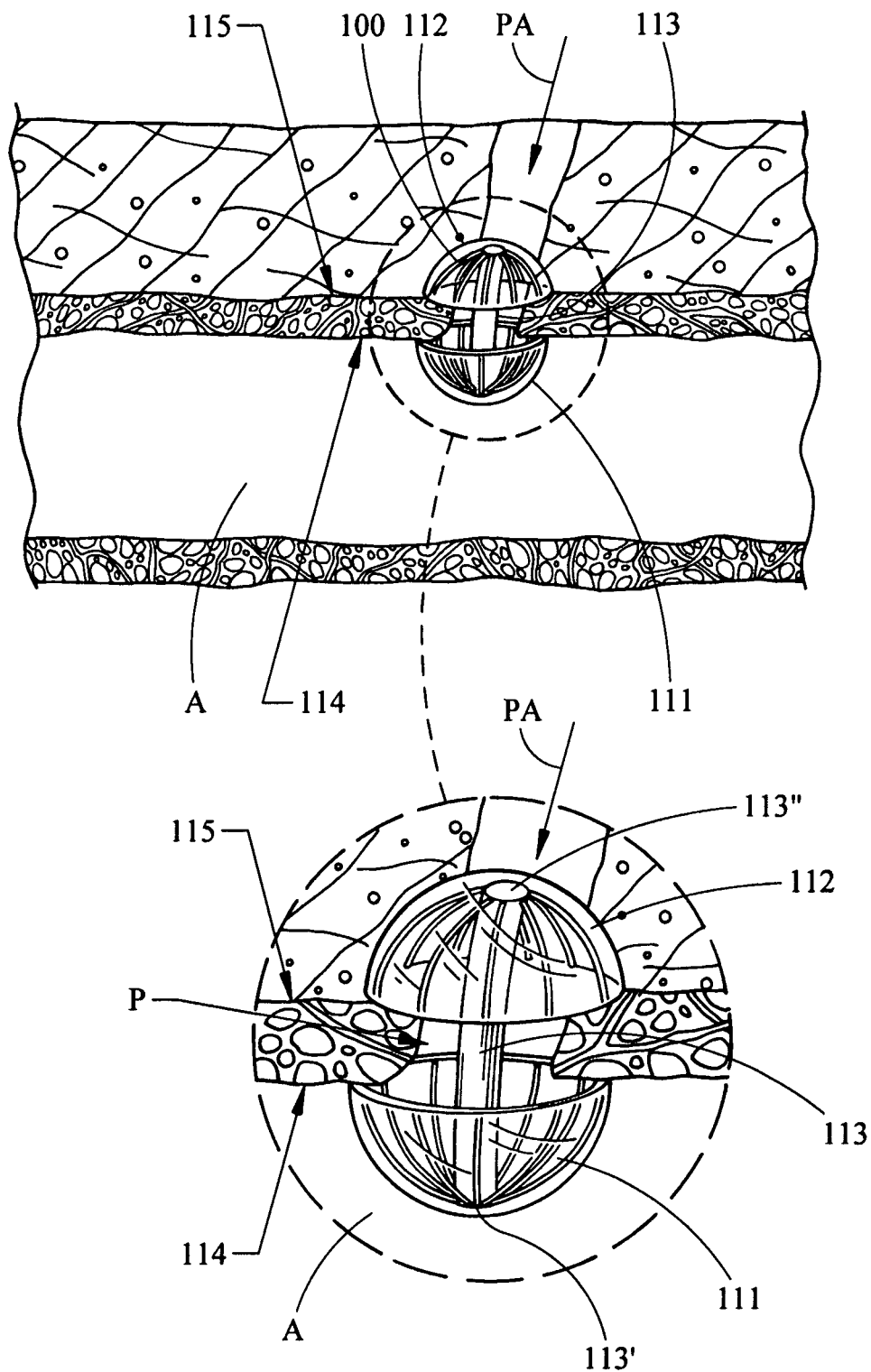
FIG. 2 is a schematic illustration of one embodiment of the medical device of the present invention.

Referring to FIG. 2, the structural member 100, which can be in a first collapsed configuration for delivery and in a second expanded configuration once deployed at the puncture P or the opening, comprises a rod 113 having a distal 113' end and a proximal end 113"; a first obstructing body 111 disposed on the distal end 113' of the rod 113; and a second obstructing body 112 disposed on the proximal end 113" of the rod 113. The first and the second obstructing bodies are opposing each other once the structural member is in the expanded configuration. The first obstructing body is affixed against an inner surface 114 of a wall of a blood vessel or a wall of a body cavity and the second obstructing body is affixed against an outer 115 (i.e., exluminal) surface of a wall of a blood vessel or a wall of a body cavity, so that the puncture P is contained between the first and the second obstructing bodies 111 and 112.

In some embodiments of the present invention, the structural member includes a first obstructing body, a rod, and a second obstructing body that can be positioned at different locations along the rod to provide adjustability to the overall medical device. In use, this adjusting the second obstructing body may be effective to seal the opening. Such a second obstructing body may be translatable along the rod, and in some embodiments, may be received over and slid along the rod so that the distance between the first obstructing body and the second obstructing body may be adjusted depending on the puncture or an opening to be closed.

The second obstructing body may be secured to the rod using any suitable method.

The rod, and the first and second obstructing bodies of the structural member of the present invention may be formed as an integral unit (e.g., from a single piece of biocompatible material), or alternatively, any component(s) of the structural member may be formed separately and then combined together, for example, using an adhesive, sutures, mechanical fastener(s), and/or any other suitable joining means. When formed separately, the structural member components may or may not be comprised of the same biocompatible material(s). In certain preferred aspects, the components are comprised of a biodegradable material, such as those described below. However, it should be noted that, in certain aspects, the components are formed from separate pieces of material, yet are retained in association with one another without the use of any other device or material (e.g., sutures, an adhesive, etc.). For example, the obstructing body(ies) and a rod may be held together by having at least one member (or any portion thereof) received around, through, over, etc., the other member (or any portion thereof). Accordingly, it is within a scope of the present invention for the rod to include a ridge or a groove to allow joining of the obstructing body(ies) to the rod. In one embodiment, the structural member comprises a rod and two obstructing bodies, wherein the obstructing bodies are formed separately from the rod and are attached to opposite ends of the rod, e.g., before or during an implantation procedure. The components of the present invention, whether formed separately or together as a single unit, can be constructed in any suitable manner, for example, using any of the processes known in the art.

The first and the second obstructing bodies may be any suitable expandable medical devices, and especially medical devices shown in FIG. 3A-E. Exemplary medical devices for use as obstructing bodies according to this invention include expandable and collapsible baskets (FIG. 3A), including discs (FIG. 3B); prongs (FIG. 3C-D); circular or oval frames (not shown); plugs; a combination of any of these (FIG. 3E), or any other suitable device known to those skilled in the art. In addition, the obstructing bodies may be in a shape of a cone, sphere, hemisphere, trumpet-shape, polygon, or any other suitable shape.

Preferably, the diameter of the obstructing bodies in the expanded configuration is about 5 mm to about 100 mm; more preferably the diameter is about 5 mm to about 50 mm. Other diameters of the obstructing bodies are also contemplated and will depend on the intended use of the medical device.

The obstructing bodies are preferably made from wires of a superelastic or shape memory alloy, such as Nitinol, a nickel-titanium alloy. The wires may also be made from other shape memory metals, such as alloys of Cu—Zn—Al or Cu—Al—Ni. Other materials are also contemplated. In order to keep the size of the obstructing bodies and the diameter of the rod narrow, very thin wires are preferred, such as wires having a diameter of about 0.0025 inches (about 0.063 mm). However, thin wires are also contemplated. Round wires are preferred, but wires of any shape may be used, including rectangular wire, square wire, wedge or "pie-shaped" wire, flat wire and triangular wire. Each "wire" in reality may comprise two or more wires twisted together for greater stiffness and control of the device.

As is well known in the art, the wires may be formed into a desired shape and heat treated or "trained" into that shape by heating to a certain temperature for a certain length of time. Typically, temperatures in the range of 500-540° C. and times from 1-5 minutes are used. Other temperatures and times may also be used. Shape-memory or superelastic materials are heat treated or annealed from a weak (martinsite) structure to a strong (austenite) structure. The alloys are weak and deformable in the martinsitic state, which is thus useful for forming the elements of the structural member. After transformation to the strong or austenitic state, they exhibit a superelastic property so long as the material remains above a transformation temperature, at which temperature it will revert to the martinsitic state. The transformation temperature may be desirably a low temperature, well below the temperature of a human body, and preferably below room temperature, which is about 20-25° C. The transformation temperature of the wires and the obstructing body may thus be selected to be below the operating temperature of the obstructing body, thus keeping the obstructing body in a superelastic state. In this state, the wires advantageously return to their original, unstressed shape when deforming stresses are removed. The superelastic wire alloy also increasingly resists deformation as the stress load is increased. Thus, when a superelastic obstructing body is collapsed and placed into a catheter or a sheath, the wires forming the obstructing body are placed into a state of stress. When the obstructing bodies are deployed, the stresses are removed, and the wires return to the desired shape of an obstructing body.

The obstructing bodies may be formed by shaping the wires and loops into the desired shape at room temperature or below, preferably with a cold mandrel, and then annealing the properly-shaped obstructing body at the proper annealing temperature for a time sufficient for the transformation to a superelastic state.

The obstructing bodies used in this invention may be made, for example, from a metal fabric by deforming a metal fabric to generally conform to a molding surface of a molding element and heat treating the fabric to substantially set the fabric in its deformed state.

When forming these obstructing bodies from a resilient metal fabric a plurality of resilient strands may be provided, with the wires being formed by braiding to create a resilient material which may be heat treated to substantially set a desired shape. This braided fabric may then be deformed to generally conform to a molding surface of a molding element and the braided fabric may be heat treated in contact with the surface of the molding element at an elevated temperature. The time and temperature of the heat treatment may be selected to substantially set the braided fabric in its deformed state. After the heat treatment, the fabric may be removed from contact with the molding element and will substantially retain its shape in the deformed state. The braided fabric so treated defines an expanded state of a medical device which may be deployed through a catheter into a channel in a patient's body.

The obstructing bodies used in this invention can also be made from a biodegradable polymer material. Examples of biodegradable materials are provided below with respect to the rod component of the structural member. The obstruction bodies of this invention can also be made from a biologic material, such as a reconstituted or naturally derived collagenous material, including submucosal tissue, such as SIS, which is described below in connection with the sealing material.

Suitable exemplary obstructing bodies are described below.

Figure 3A:
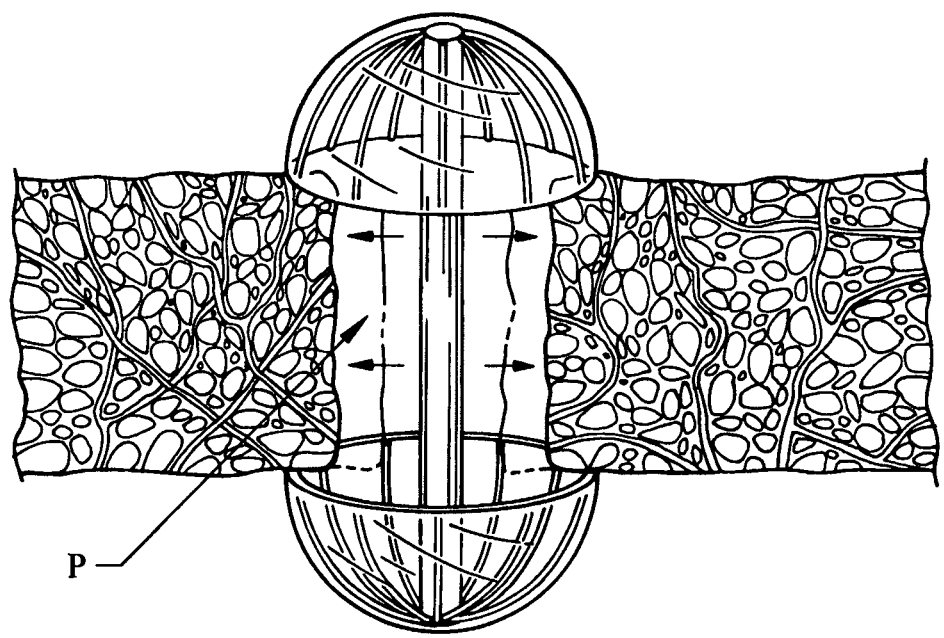
FIGS. 3A-E are schematic illustrations of exemplary structural members.
Figure 3B:
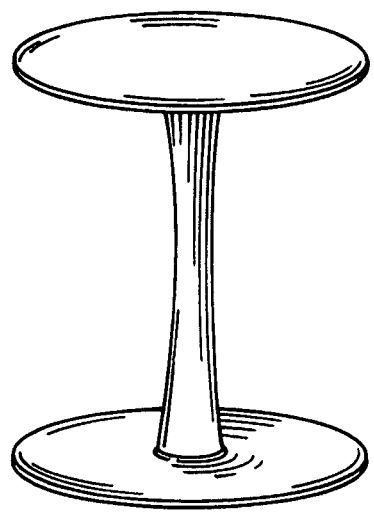
Figure 3C:
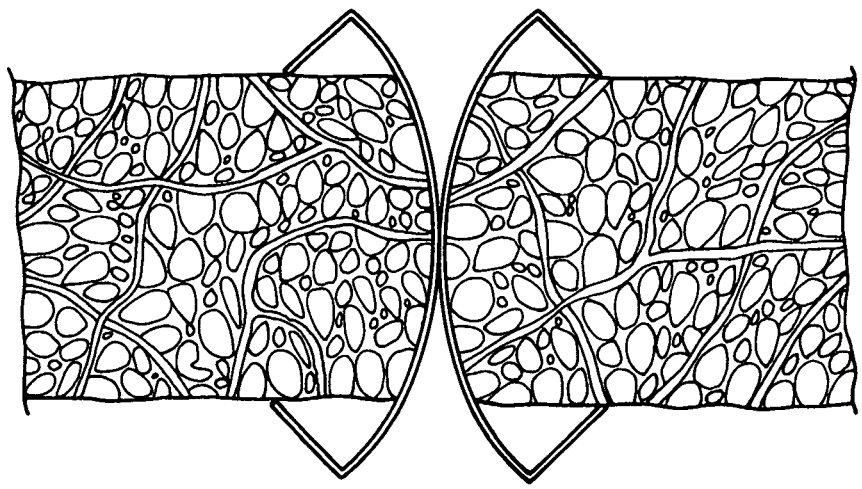

In one example, the obstructing bodies may be expandable and collapsible baskets (FIGS. 3A-3B). Baskets are known in the retrieval art and are commonly used to remove an object, such as a stone or other undesirable object, from a body cavity. Examples of baskets were previously described in U.S. Pat. No. 5,725,552, disclosure of which is incorporated herein in its entirety. U.S. Publication No. 2003/0171772 A1, disclosure of which is incorporated herein in its entirety, specifically discloses examples of collapsible baskets.

Baskets for sealing a puncture or an opening according to this invention may be made from tubular mesh, which may be compressed for delivery through catheter (collapsed configuration) but which, on delivery, expand into an "umbrella", "flat," "disc-like," or other suitable shape (expanded configuration) appropriate for sealing the puncture or the opening. Accordingly, preferred baskets for use in this invention may have a collapsed configuration and an expanded configuration.

The metal fabric from which the basket may be formed may comprise a plurality of wire strands that may be woven or braided into a tubular configuration and then heat set in a mold in a manner described in U.S. Pat. No. 6,123,715, the contents of which are hereby incorporated by reference.

Figure 4:
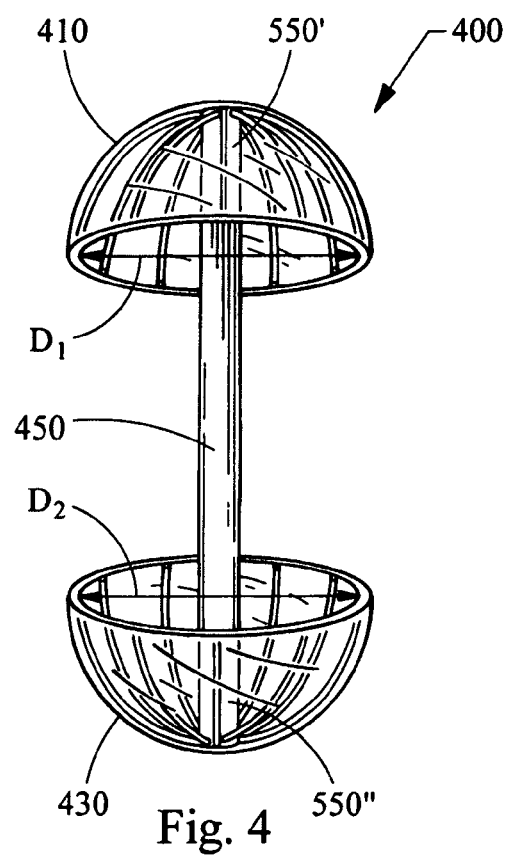
FIG. 4 is a schematic illustration of another embodiment of the medical device of the present invention.

As illustrated in FIG. 4, the structural member 400, in its unconstrained state, comprises a first basket 410 having a predetermined first expanded diameter D1; a second basket 430 also having a predetermined second expanded diameter D2; and a rod 450 having a distal end 550' and a proximal end 550", wherein the first basket 410 is disposed on the distal end 550' of the rod 450 and the second basket 430 is disposed on the proximal end 550" of the rod 450.

The expandable and collapsible baskets may also comprise a plurality of loops attached to a rod, the loops interleaved and formed into an atraumatic periphery of the baskets.

Figure 5A:
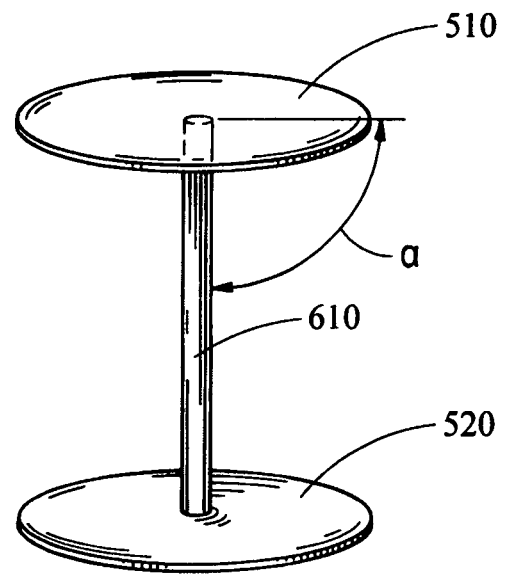
FIG. 5A is a schematic illustration of an exemplary structural member.

As mentioned above, the expandable and collapsible baskets may be discs. As illustrated in FIG. 5A, one preferred characteristic of the obstructing bodies 510 and 520 of this invention is that when the device is in its expanded configuration, the obstructing bodies 510 and 520 are flat or the disc-like and form about 90 degrees angle with the rod 610 in the center of the obstructing bodies. Once placed in the puncture site, this angle allows to close the puncture and to minimize the entry of any contaminants or foreign material through the puncture and into a vessel or a body cavity. Although this obstructing body configuration is preferred, not all obstructing bodies will form 90 degrees angle with the rod. These types of obstructing bodies are also included within the scope of this invention.

Figure 5B:
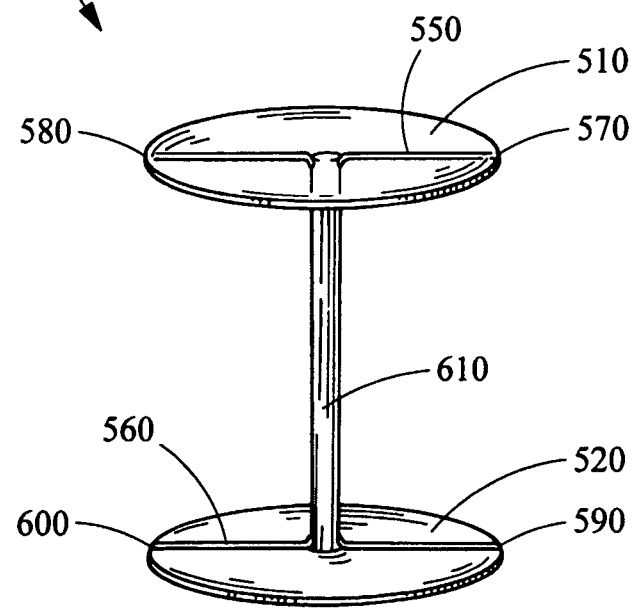
FIG. 5B is another illustration of an exemplary structural member.

In yet another embodiment, as illustrated in FIG. 5B, the structural member 500 may include obstructing bodies 510 and 520 that are circular or oval metal frames 530 and 540 with metal wires 550 and 560 connecting the opposing ends 570 and 580 and opposing ends 590 and 600 of the two frames. The metal wires may also connect the frames 530 and 540 to the rod 610.

Figure 3D:
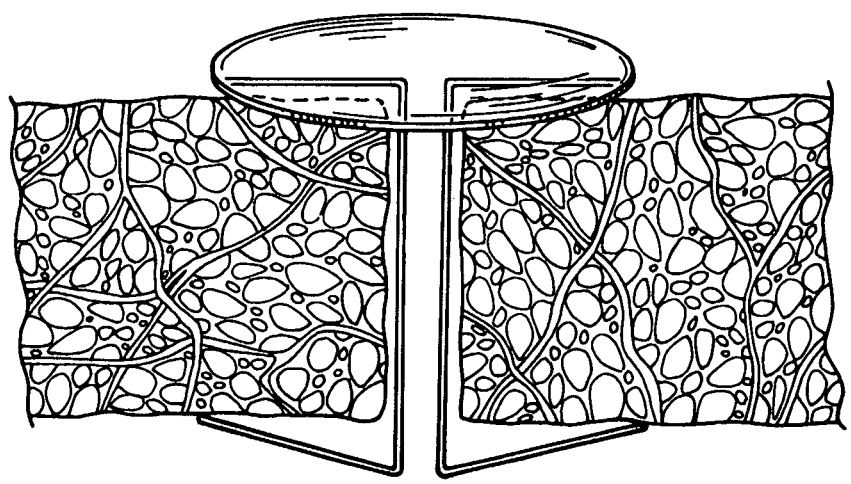
Figure 3E:
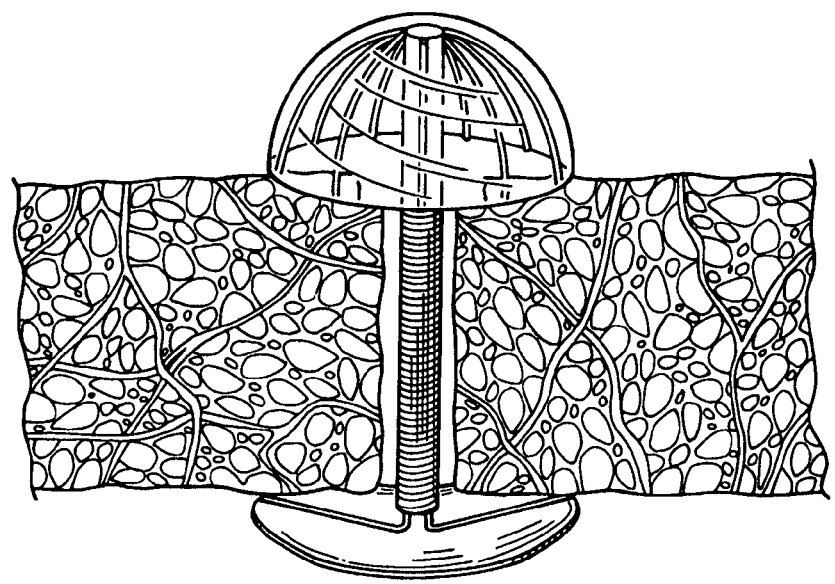

In another embodiment, the obstructing bodies may be prongs (FIG. 3D-E).

In yet another embodiment, the obstructing bodies may be plugs.

In a further embodiment, the obstructing bodies may include apertures, holes or the like.

According to this invention, the obstructing bodies described herein are disposed on a rod. A "rod" refers to a center portion of a structural member and it may include a rod, tube, a string, a thread, or a series of wires, which are braided or loose, or otherwise brought together.

The rod may be a solid Nitinol rod or tube, or may be a stainless steel shaft or tube. Nitinol is preferred. The rod may instead be a number of stranded or non-stranded wires, depending on the degree of flexibility desired. Joining portion may simply be a separate hollow cannula or a hollowed-out portion at the ends of the rod.

In another embodiment, the rod may be made from biodegradable polymer material. Examples of such biodegradable polymers include, but are not limited to, hydrogels (Temenoff, J. S. et al., "Effect of poly(ethylene glycol) molecular weight on tensile and swelling properties of oligo(poly(ethylene glycol)fumarate) hydrogels for cartilage tissue engineering" *J. Biomed. Mater. Res.* 59, 429-437 (2002), Lee, K. Y. et al. "Controlling mechanical and swelling properties of alginate hydrogels independently by cross-linker type and cross-linking density" *Macromolecules* 33, 4291-4294 (2000)), elastin-like peptides (van Hest, J. C. M. & Tirrell, D. A., "Protein-based materials, toward a new level of structural control" *Chem. Comm.* 19, 1897-1904 (2001), Welsh, E. R. & Tirrell, D. A., "Engineering the extracellular matrix: a novel approach to polymeric biomaterials. I. Control of the physical properties of artificial protein matrices designed to support adhesion of vascular endothelial cells" *Biomacromolecules* 1, 23-30 (2000) and Urry, D. W. et al., "Elastic protein-based polymers in soft tissue augmentation and generation" *J. Biomater. Sci., Polym.* Ed. 9, 1015-1048 (1998)), and polyhydroxyalkanoates (PHAS) (Poirier, Y. et al., "Production of polyhydroxyalkanoates, a family of biodegradable plastics and elastomers, in bacteria and plants" *Bio/Technology* 13, 142-150 (1995) and Sodian, R. et al. "Fabrication of a trileaflet heart valve scaffold from a polyhydroxyalkanoate biopolyester for use in tissue engineering" *Tissue Eng.* 6, 183-187 (2000)).

Suitable biodegradable polymers also include, but are not limited to, polylactides (PLA) (including isomers of PLA and combinations thereof), poly (D,L-lactide) (PDLA), poly-L-lactic acid (PLLA), polyglycolides (PGA), poly(ethylene glycol) (PEG), poly(lactide-co-glycolides) (PLGA), polyanhydrides, polyorthoesters, and block copolymers of these compounds. Other suitable biodegradable polymers include, but are not limited to polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), poly(D,L-lactide-co-caprolactone) (PLA/PCL), poly(glycolide-co-caprolactone) (PGA/PCL), poly(phosphate ester), poly(amino acid) and poly(hydroxy butyrate), polydepsipeptides, maleic anhydride copolymers, polyphosphazenes, polyiminocarbonates, poly[(97.5% dimethyl-trimethylene carbonate)-co-(2.5% trimethylene carbonate)], cyanoacrylate, polycyanoacrylates, polyethylene oxide, hydroxypropylmethylcellulose, polysaccharides (such as hyaluronic acid, chitosan and regenerate cellulose), and proteins (such as gelatin and collagen).

Another biodegradable polymer suitable for use in the present invention is poly(glycerolsebacate) (Wang, Y., et al. "A tough biodegradable elastomer" Nature Biotechnology 20, pp. 602-606 (2002)). In one embodiment, such a polymer prepared using about a 1:1 ratio of glycerol/sebacic acid yields a biodegradable polymer capable of large reversible deformations.

Bioremodelable materials, such as ECM material, including SIS may not be used to form the rod component of the structural member.

Figure 10A:
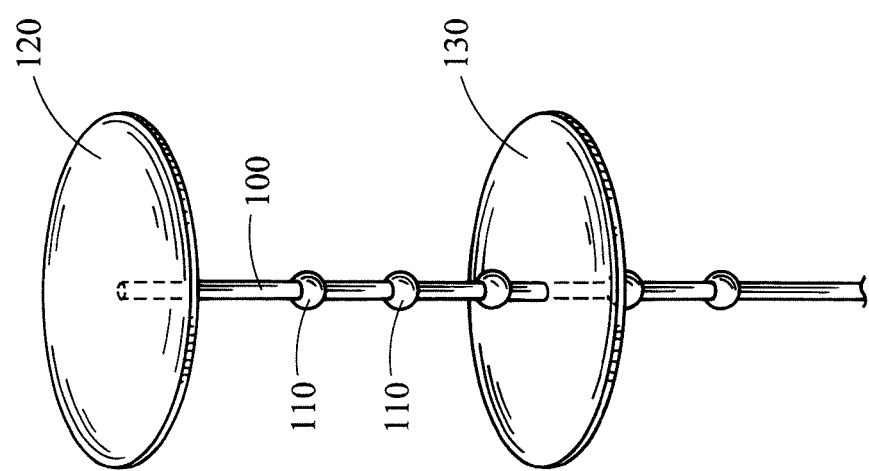
FIGS. 10A-D are schematic illustrations of various rod configurations including structural elements.
Figure 10B:
Figure 10C:
Figure 10D:

The rod may have various configurations, which are illustrated in FIGS. 10A-D. As shown in FIG. 10A, at least a portion of the rod 100 may include beads 110. As shown in FIGS. 10B and 10C, at least a portion of the rod may be in a form of a 'tie-wrap.' As shown in FIG. 10D, the rod or at least a portion of the rod may have a form of oriented fibers. These beads, fibers or tie-wrap-like elements may be integral with the rod or may be separate structures that are attachable to the rod 100 in a permanent or non-permanent manner.

The presence of these structural elements with the rod 100 allows for adjusting the distance between a first obstructing body 120 and the second obstructing body 130 once the structural member is placed at the puncture. For example, once the device of this invention is deployed at the puncture, the second obstructing body 130 may be pushed against the wall of the vessel or the body cavity by sliding the second obstructing body 130 over the beads 110. A bead 110 will provide a resistance and will prevent the second obstructing body 130 from retracting backwards or disengaging the wall.

Figure 11:
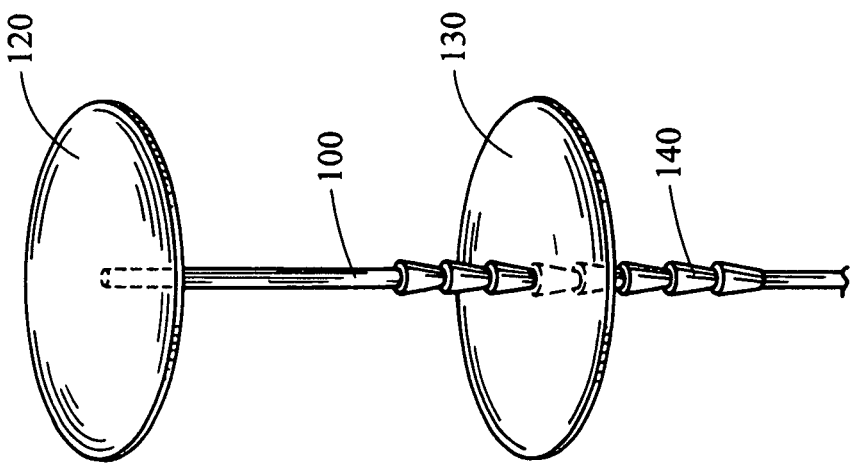
FIG. 11 is another schematic illustration of a rod configuration.

In one embodiment shown in FIG. 11, a portion of a rod 100 includes a 'tie wrap' 140 that allows the second obstructing body 130 to be secured in place once deployed at the puncture.

It is desirable for the rod to have a length of at least about 0.1 centimeters, and in many situations at least about 0.2 to about 5 centimeters. In illustrative embodiments, the rod has a length of from about 0.2 to about 2 centimeters, or most preferably, from about 0.2 to about 1 centimeter. Additionally, in certain embodiments, the rod will have a diameter, which may or may not be constant along the length of the graft body, but preferably is constant, of from about 0.1 to about 10 millimeters, or more typically from about 0.1 to about 5 millimeters.

The obstructing bodies may be joined to the ends of the rod by one or more of several means, including in permanent or non-permanent manner. For example, if the obstructing bodies are metal baskets, the ends of the wire strands forming the metal baskets may be attached to one another to prevent the fabric from unraveling by a clamp. The clamp may be cylindrical in shape. The obstructing bodies may also be attached to the rod by other methods, such as by welding, soldering, brazing, use of a biocompatible cementitious material or in any other suitable fashion.

A medically-acceptable adhesive may also be used to dispose or join the obstructing bodies to the rod. Loctite® 4011 cyanoacrylate may be used for this application.

Where the obstructing body is affixed in a non-permanent manner, such as by absorbable adhesive, the obstructing body may detach from the structural member after a certain period of time, by which time the puncture has closed. The timing of the release of the obstructing body may vary, depending upon the thickness and dissolution characteristics of the material used for attaching the obstructing body to the rod. Desirably, the length of time elapsed before the obstructing body detaches is about 1 to about 8 weeks, more desirably about 2 to about 6 weeks, and even more desirably about 4 weeks.

2. Sealing Material

The medical devices of this invention also include a sealing material associated with the structural member. Preferably, the sealing material is a foam material, which may be capable of absorbing blood to expand several times (e.g., 6-10x) its diameter and to restore hemostasis and enhance tissue ingrowth. Another advantage of including the sealing material with the device is that the sealing material may further enhance the sealing provided by the structural member described above.

The sealing material may be associated with the structural member by various methods, including by lining, weaving, attaching, wrapping, gluing and other suitable methods.

Figure 6A:
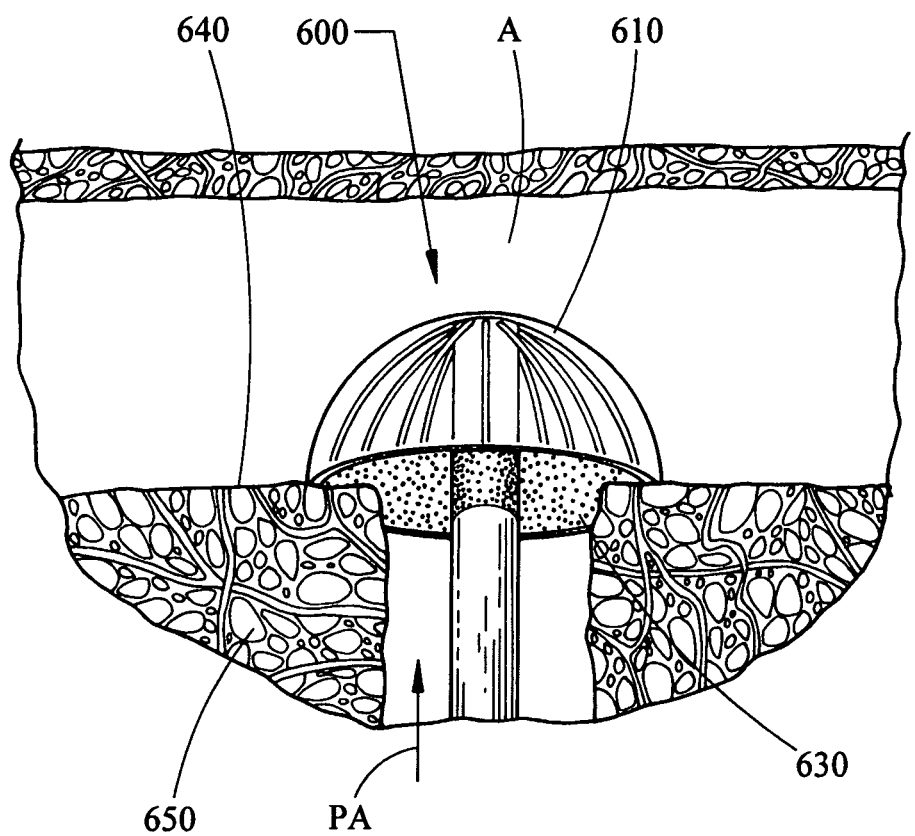
FIG. 6A is a schematic illustration of a obstructing body lined with a sealing material.
Figure 6B:
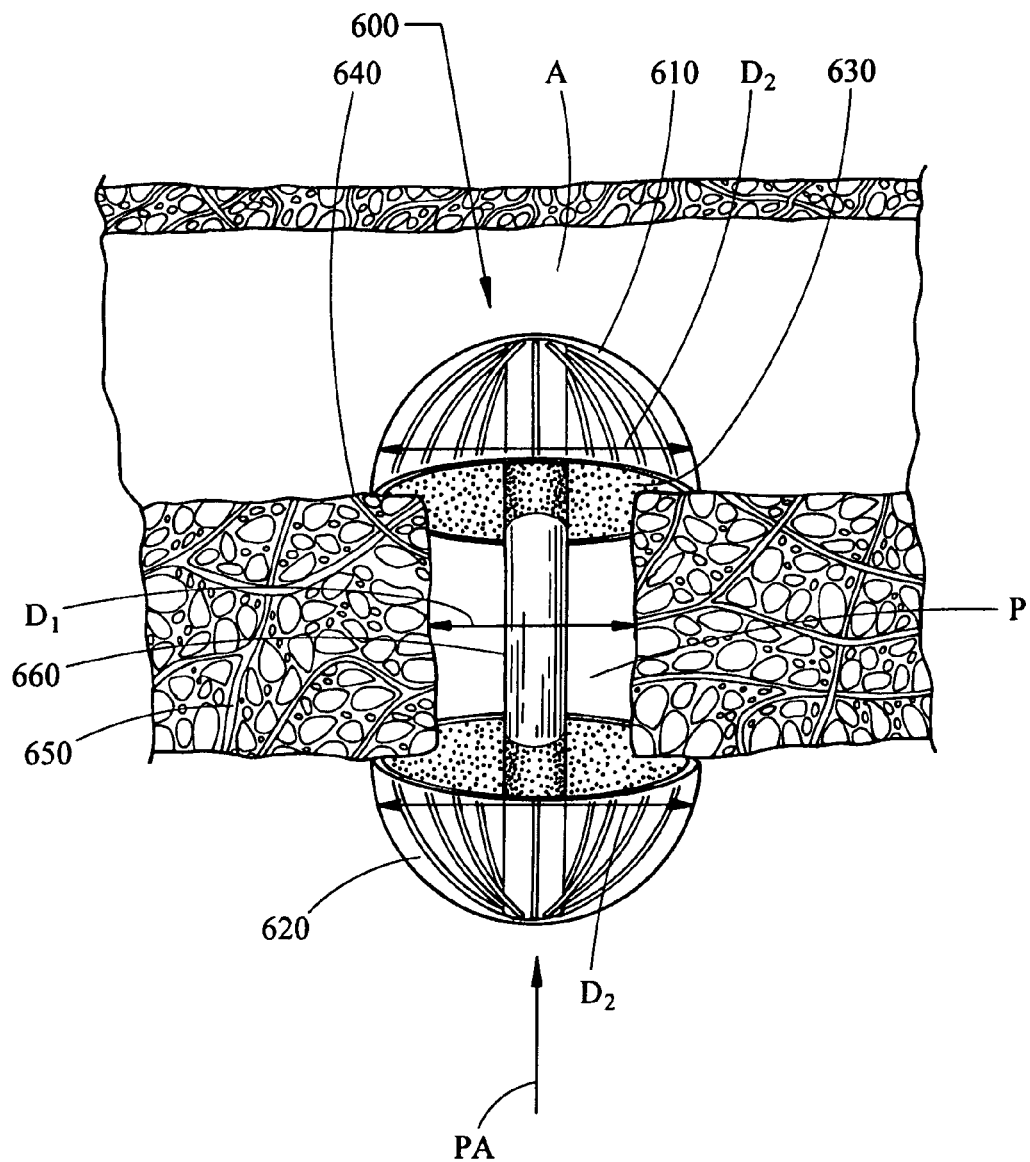
FIG. 6B is a schematic illustration of a structural member having two obstructing bodies lined with a sealing material.

In certain embodiments, the sealing material may be attached to or lining at least a portion of at least one element of the structural member 600 (FIGS. 6A and 6B). For example, the sealing material may be lining the inner side 630 of the obstructing body 610 of the structural member 600, having diameter D2, as shown in FIG. 6A. As further illustrated in that figure, the sealing material may be lining the obstructing body 610 so that once the obstructing body 610 is affixed against the inner surface 640 of a wall 650 of a blood vessel A or a wall of a body organ, the sealing material forms at least one layer (not shown) between the wall 650 of a blood vessel A and the first obstructing body 610. The sealing material may be lining both obstructing bodies 610 and 620 (having diameter D1), as illustrated in FIG. 6B. The rod is shown with 660.

Figure 6C:
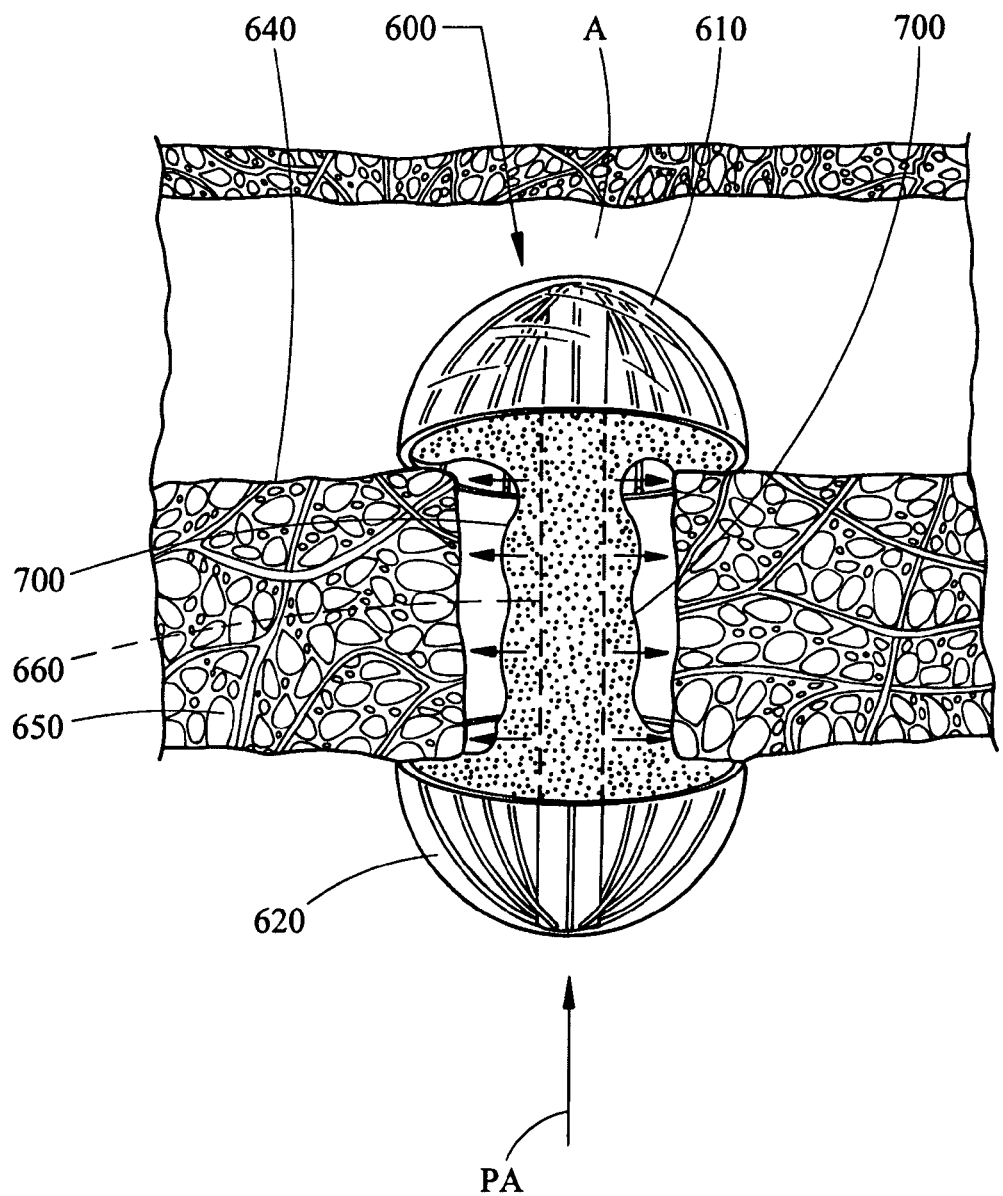
FIG. 6C is a schematic illustration of a structural member having the rod wrapped in a sealing material.

In another embodiment shown in FIG. 6C, the sealing material 700 may be attached to the rod 660 connecting the first obstructing body 610 and the second obstructing body 620 of the structural member 600. Alternatively or in addition, the sealing material may be wrapped around the rod 660.

In yet another embodiment, the sealing material may be attached or otherwise incorporated into all three components of the structural member (not shown).

Figure 12:
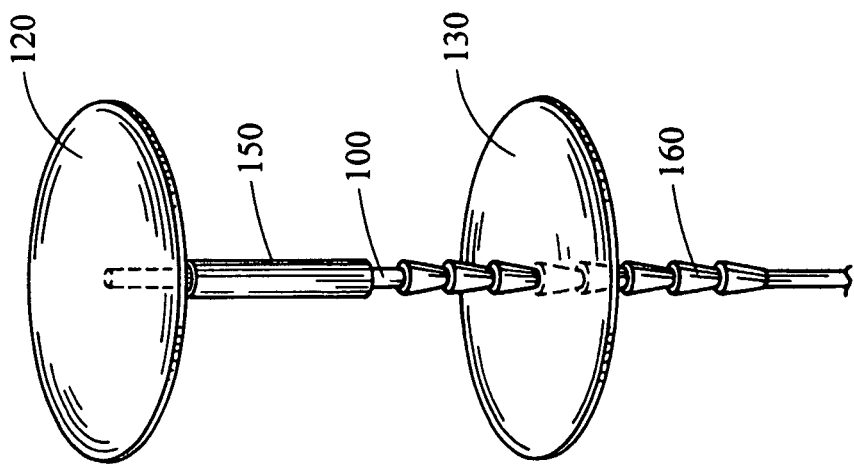
FIG. 12 is an exemplary illustration of a medical device of this invention.

In another embodiment illustrated in FIG. 12, the sealing material 150 may be wrapped around at least a portion of the rod 100. Another portion of the rod may include structural elements 160, such as a "tie wrap"-like elements for adjusting the distance between obstructing bodies 120 and 130.

In a further embodiment, the sealing material may be injected into a space between the two obstructing bodies after positioning of the structural member at the puncture and before adjusting the distance between the first and the second obstructing bodies and sealing off the opening. In this embodiment, the sealing material preferably polymerizes once injected in the space between the two obstructing bodies.

Upon placing the medical device at the puncture, the sealing material may absorb blood to expand (FIG. 6C, arrows) several times (e.g., 6-10×) its diameter and to cause hemostasis. This expansion further enhances the sealing provided by the structural member.

Preferably, the sealing material may include a reconstituted or a naturally-derived collagenous material, such as ECM material. The sealing material is provided for enhancement of sealing at the puncture site by expanding at the puncture.

ECM Material

It is advantageous to use a remodelable material for the sealing material of the present invention, and particular advantage may be provided by including a remodelable collagenous material. Such remodelable collagenous material can be provided, for example, by collagenous materials isolated from suitable tissue source from a warm-blooded vertebrate, and especially a mammal. Such isolated collagenous materials may be processed so as to have remodelable properties and promote cellular invasion and tissue infiltration. Remodelable materials may be used in this context to promote cellular growth or ingrowth at the puncture, while optionally containing others materials.

Reconstituted or naturally-derived collagenous materials may be used as sealing material in the present invention. Such materials that are at least bioresorbable will provide advantage in the present invention, with materials that are bioremodelable and promote cellular invasion and ingrowth providing particular advantage.

Suitable bioremodelable materials may be provided by collagenous extracellular matrix materials (ECMs) possessing biotropic properties, including in certain forms angiogenic collagenous ECMs. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Submucosa or other ECM materials may be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics or thrombus-promoting substances such as blood clotting factors, e.g., thrombin, fibrinogen, and the like. These substances may be applied to the ECM material as a premanufactured step, immediately prior to the procedure (e.g., by soaking the material in a solution containing a suitable antibiotic such as cefazolin), or during or after delivery of the material in the patient.

Submucosa or other ECM tissue used in the invention is preferably highly purified, for example, as described in U.S. Pat. No. 6,206,931. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 μg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

Preferred type of submucosa for use in this invention is derived from the intestines, more preferably the small intestine, of a warm blooded vertebrate; i.e., small intestine submucosa (SIS). SIS is commercially available from Cook Biotech, West Lafayette, Ind.

Preferred intestine submucosal tissue typically includes the tunica submucosa delaminated from both the tunica muscularis and at least the luminal portions of the tunica mucosa. In one example the submucosal tissue includes the tunica submucosa and basilar portions of the tunica mucosa including the lamina muscularis mucosa and the stratum compactum. The preparation of intestinal submucosa is described in U.S. Pat. No. 4,902,508, and the preparation of tela submucosa is described in U.S. Pat. No. 6,206,931, both of which are incorporated herein by reference. The preparation of submucosa is also described in U.S. Pat. No. 5,733,337 and in 17 Nature Biotechnology 1083 (November 1999); and WIPO Publication WO 98/22158, which is the published application of PCT/US97/14855. Also, a method for obtaining a highly pure, delaminated submucosa collagen matrix in a substantially sterile state was previously described in U.S. Publication No. 2004 0180042 A1, disclosure of which is incorporated by reference.

The ECM material for use in the present invention may be processed to provide preferred shape or form of the ECM material.

For example, the ECM material may take many shapes and forms, such as coiled; helical; spring-like; randomized; branched; sheet-like; tubular; spherical; fragmented; powdered; ground; sheared; fluidized; sponge-like; foam-like; and solid material shape. Foam-like and sponge-like ECM materials are preferred for use in this invention. In some embodiments, a fluidized or injectable form of the ECM material may be preferred. Preferably, the fluidized or injectable form of the ECM polymerizes once delivered to the puncture or the opening.

Most preferably, the sealing material is a foam-like material, such as an extracellular matrix material such as SIS sponge material comprising lyophilized and comminuted SIS that has been formed into a thin layer and cross-linked using one of several known cross-linking agents. It is the highly-absorbent sponge material is capable of expanding radially and to completely seal a puncture of an opening.

Specific examples of preferred materials for use as sealing material of this invention include lyophilized SIS sponge or other ECM materials, non-extracellular collagen sponge (such as bovine-derived collagen), or synthetic hemostatic materials such as GELFOAM® (Pharmacia Corporation, Peapack, N.J.).

In one illustrative embodiment, the sealing material includes a small square (e.g., 2-3 cm) of sheet of sponge comprising lyophilized and cross-linked SIS, typically about 1 mm in thickness. This sheet of sponge may be wrapped around the rod component of the structural member. Animal studies suggest that the illustrative sealing material can be used to effectively seal vessel punctures made by introducer sheaths having an O.D. up to 16 Fr. While naturally derived biomaterials, particularly bioremodelable materials like SIS described above, are generally preferred for use as the sealing material of this invention, synthetic materials, including those into which growth factors are added to make them bioremodelable, are also within the scope of this invention.

Method of Sealing

The invention is a method of sealing a puncture or an opening through tissue, a wall of a blood vessel or a wall of a body cavity or a general hole in tissue. In general, the method includes deploying a medical device comprising a structural member and a sealing material associated with the structural member though a delivery member as described herein below. The medical device may be deployed into the blood vessel or body cavity though the puncture, wherein components of the structural member radially expand and assume an expanded configuration following the deployment and wherein the sealing material enhances sealing of the puncture. The remaining details of the method relate to the method of delivering the medical device of this invention as described below.

Figure 7:
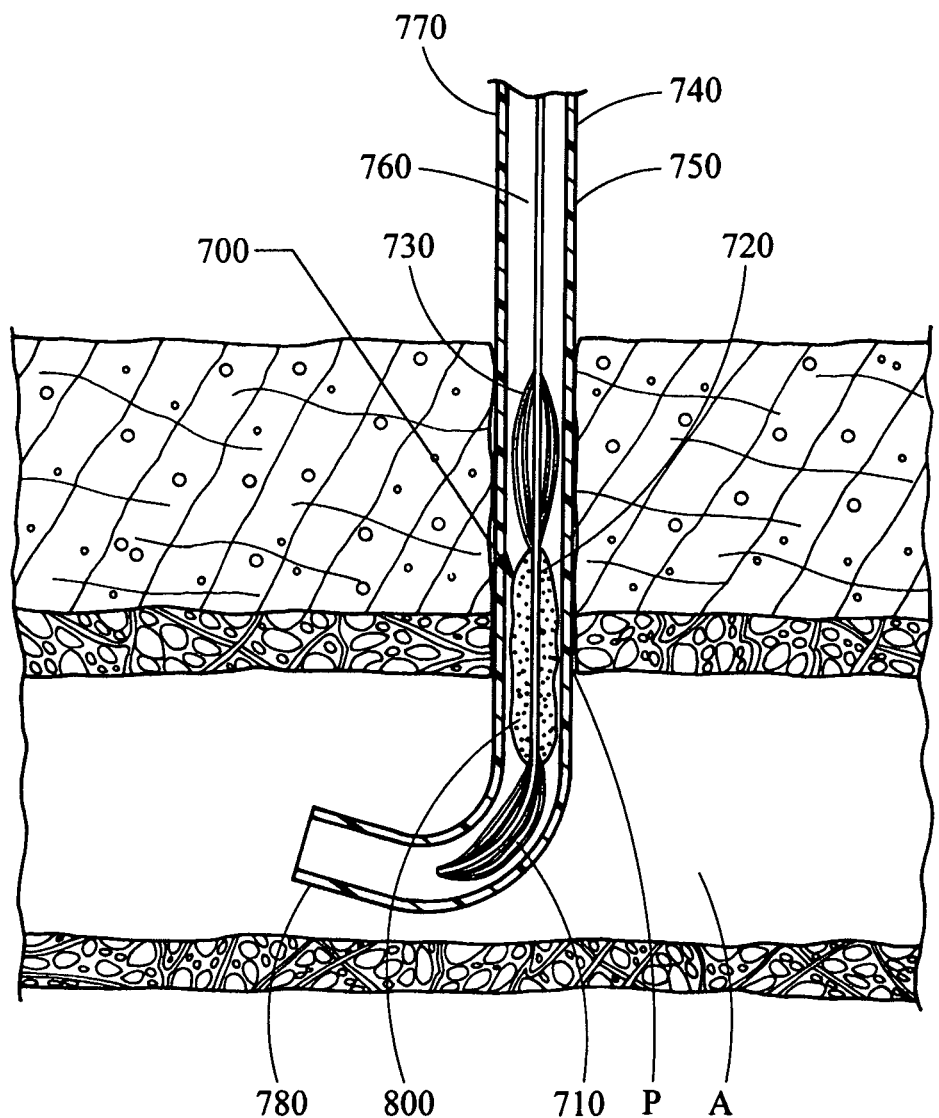
FIG. 7 is a schematic illustration of a delivery member and deployment of the medical device of this invention.

Referring to FIG. 7, a first obstructing body portion 710 of the structural member 700 connected by a rod 720 to a second obstructing body portion 730 of the structural member formed in a predetermined shape and made in accordance with the process outlined herein, can be collapsed and inserted into a lumen of a delivery member 740, as shown in FIG. 7. A delivery member 740 may take any suitable shape, but desirably comprises a catheter comprising a body 750 having at least one lumen 760 extending longitudinally therein. The lumen extends longitudinally through the catheter body 750 from its proximal end 770 to an exit port at its distal end 780. The lumen 760 of the catheter 740 may be adapted for delivering the medical device of this invention, comprising a structural member 700 and a sealing material 800, into a puncture P in a wall of a blood vessel and positioning the medical device at the puncture P. In addition or optionally, a catheter used for delivering of the medical device of this invention may include a sheath.

Figure 8:
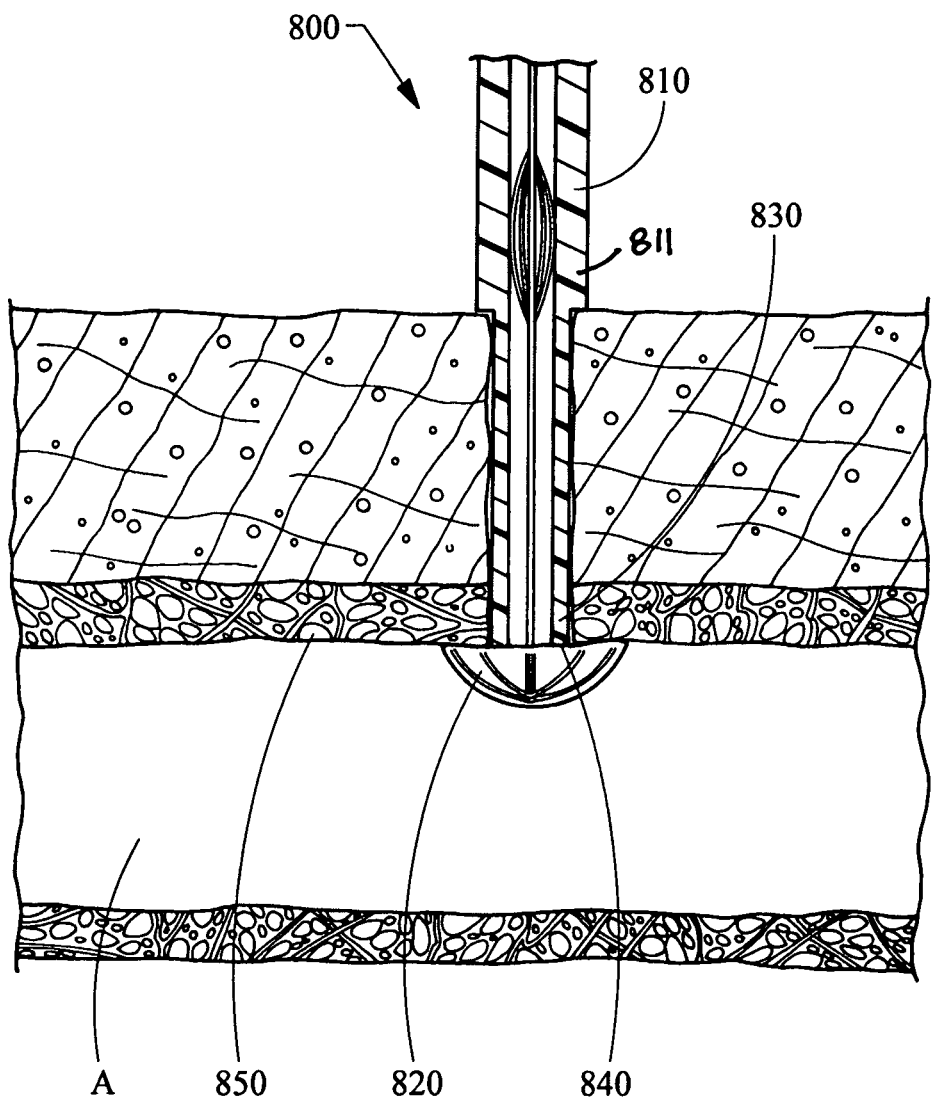
FIG. 8 is another schematic illustration of a delivery member and deployment of the medical device of this invention.

Also, as shown in FIG. 8, the catheter 810 may include a coaxial member 811, such as a collar or an umbrella-like structure to preclude the catheter from going back into the vessel following deployment and positioning of the first obstructing body of the medical device described above. An additional optional coaxial member (not shown) may be used to preclude the catheter from going back through the puncture following deployment and positioning of the second obstructing body of the medical device. The coaxial member(s) may be adjustable in size. Alternatively, the catheter may include a built-in profile into the catheter itself to prevent the catheter from entering the vessel following deployment and positioning of the medical device.

As shown in FIG. 8, once the medical device 800 is inserted into the delivery member 810, the device may be advanced through the lumen of a catheter 810 to extend the distal end of the rod connected to a first obstructing body 820 beyond the distal end 830 of the catheter 810 for deployment in a lumen of a tubular tissue structure A, such as a blood vessel or other structure. Once the first obstructing body 820 is deployed, the device may be retraced by retracting the catheter 810 so that the "flat" basket portion of the first obstructing body 820 of the structural member engages the wall of the vessel covering the puncture from the inside of the vessel or a body cavity.

Figure 9:
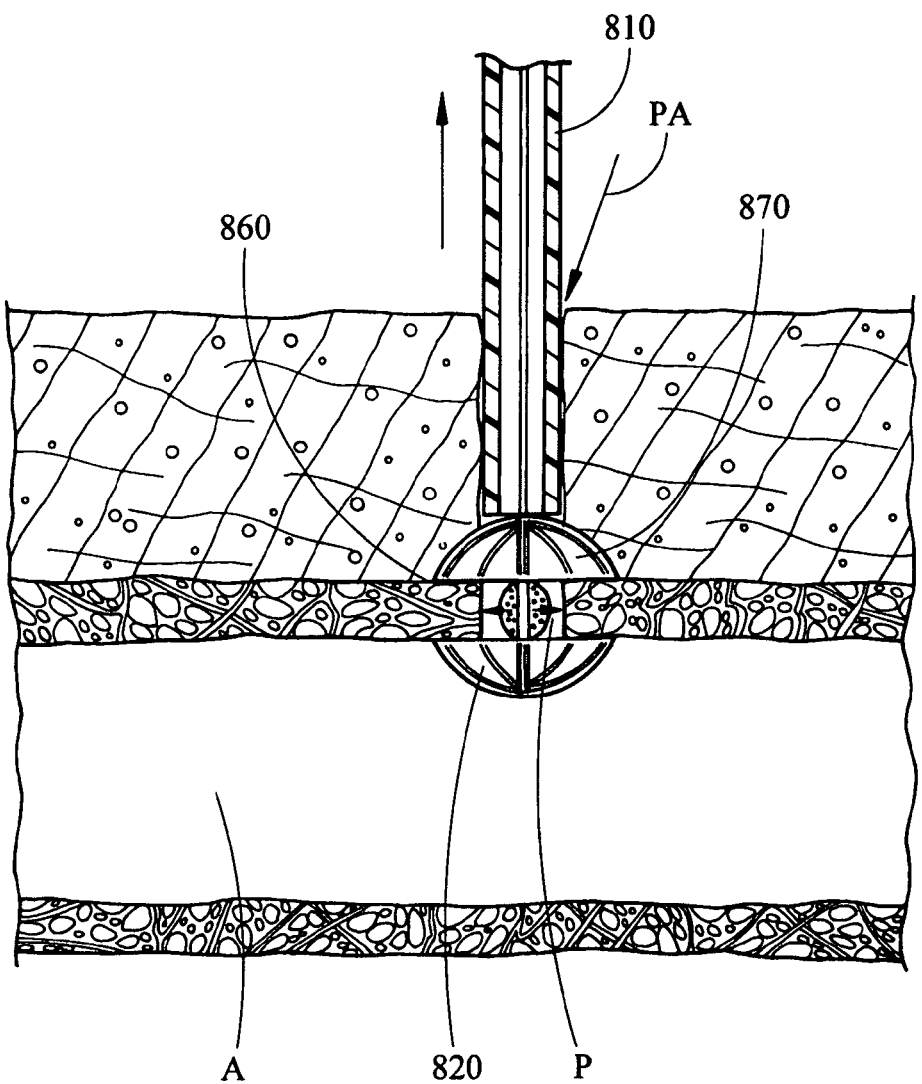
FIG. 9 is a schematic illustration of a medical device of this invention deployed at the puncture.

Referring to FIG. 9, once the proper position of the first obstructing body 820 is confirmed, the device is retraced further by retracting the catheter 810 beyond the puncture P to an area outside 860 of the vessel A though the puncture P and the proximal end of the rod is deployed though the catheter 810 in the area exterior to the vessel wall 860 (exluminal).

In one embodiment, the second obstructing body 870 may be connected to the proximal end of the rod and deployed at the same time the proximal end of the rod is deployed.

In an alternative embodiment, the second obstructing body 870 may be received over the proximal end of the rod after the proximal end of the rod is deployed. The second obstructing body is preferably configured to slide along the rod. To create such an opening through which the rod can be received, portions of the second obstructing body 870 may be cut (and in some cases removed). For example, the second obstructing body 870 may have a circular cut of a diameter of the rod. In other embodiments, cuts of other shapes may be made to provide an opening through which a rod can be received, including but not limited to, an X-shaped cut or an S-shaped cut. When an X-shaped cut is made in the second obstructing body 870, flaps may be formed. These flaps may be useful in securing second obstructing body 870 to the rod, e.g., by adhering the flap(s) to the rod.

When the second obstructing body 870 is received over the proximal end of the rod, the distance between the first and the second obstructing bodies may be adjusted appropriately to the size of the puncture or opening. The second obstructing body 870 may be pushed along the rod until resistance is achieved by engaging the wall of the blood vessel. As described above, the rod may include structural elements that may allow for adjusting the distance between the first and the second obstructing bodies. For example, the proximal end of the rod may include beads. Once the second obstructing body is slid over a bead, a bead will prevent the second obstructing body from retracting backwards and disengaging the vessel wall.

Upon exit from the delivery member 810, the first and the second obstructing bodies 820 and 870 elastically expand to substantially recover their thermally set, "remembered" shape from the heat treatment process and assume their expanded configurations. The obstructing bodies may preferably be sized so that they frictionally engage the puncture site P.

Once the device is deployed at the puncture P, the sealing material expands (horizontal small arrows) by absorbing the blood and fills in the spaces remaining at the puncture and by doing so the sealing material enhances the sealing provided by the structural member. Such positioning of the medical device allows for a complete sealing of the puncture P.

Once the device is deployed out the distal end 830 of the catheter 810, the medical device may be retained by the delivery device as shown in FIG. 9. By keeping the device attached to the delivery means, the operator may still retract the device for repositioning if it is determined that the device is not properly positioned in the first attempt. The proper positioning may be confirmed by retracting the catheter back and confirming that no blood flow occurs through the catheter 810. This threaded attachment may further allow the operator to control the manner in which the device is deployed out of the distal end of the catheter 810.

Following the delivery of the medical device and positioning it at the puncture P, the catheter 810 may be withdrawn, leaving the medical device behind. The structural member functions to seal and provide a structural support and the sealing material functions to facilitate hemostasis and/or healing of tissue at the puncture while enhancing the sealing provided by the structural member.

Other methods of placing the medical device at the puncture may also be used and will be known to those skilled in the art.

The delivery of the medical device of this invention may also occur via a rapid exchange delivery catheter. The rapid exchange delivery catheters and methods of using the rapid exchange delivery catheters were previously described in U.S. Pat. Nos. 4,762,129; 5,690,643; 5,814,061; 6,371,961; and Provisional Pat. Application, entitled "A Rapid Exchange Balloon Catheter and a Method for Making the Same," Attorney reference LHa/129969.

It is therefore intended that the foregoing detailed description be regarded as illustrative rather than limiting, and that it be understood that it is the following claims, including all equivalents, that are intended to define the spirit and scope of this invention.

The invention claimed is:

1. A medical device for immediate sealing of a puncture or an opening through a wall of a blood vessel or a body cavity, comprising:
   a) a structural member which can be in a first collapsed configuration and in a second expanded configuration, the structural member comprising
     i) an elongated member having a distal end and a proximal end, wherein at least a portion of the elongated member comprises protruding structural elements;
     ii) a first obstructing body disposed on the distal end of the elongated member and having a first obstructing body perimeter enclosing a substantially solid surface; and
     iii) a second obstructing body having a second obstructing body perimeter enclosing a substantially solid surface capable of being translated along the portion of the elongated member comprising the protruding structural elements for adjusting a distance between the first and the second obstructing bodies; and
   b) a remodelable sealing material associated with the structural member comprising a reconstituted or naturally-derived collagenous material wherein the collagenous material encourages and promotes tissue ingrowth at the puncture or the opening, wherein the sealing material is attached to or lining at least a portion of at least one of the elongated member, the first obstructing body and the second obstructing body, wherein the sealing material is substantially enclosed within the structural member once the structural member is in the expanded configuration and deployed at the puncture or the opening;
   wherein the first and the second obstructing bodies are opposing each other once the structural member is in the expanded configuration,
   wherein the first obstructing body is configured to be affixed against an inner surface of the wall of the blood vessel or body cavity so that at least the first obstructing body perimeter is in a continuous contact with the inner surface of the wall of the blood vessel or body cavity and the second obstructing body is configured to be affixed against an outer surface of the wall of the blood vessel or body cavity so that at least the second obstructing body perimeter is in a continuous contact with the outer surface of the wall of the blood vessel or body cavity, once the structural member is in the expanded configuration and deployed at the puncture or the opening to immediately seal the puncture or the opening and substantially prevent leakage through the puncture or the opening, and
   wherein the first and the second obstructing bodies are configured to biodegrade or detach following the tissue ingrowth and the closure of the puncture or opening.

2. The device of claim 1, wherein the first obstructing body is selected from the group consisting of a plug, an expandable and collapsible basket, a disc; and the second obstructing body is selected from the group consisting of a plug, an expandable and collapsible basket, a disc.

3. The device of claim 1, wherein the first obstructing body is a plug, and the second obstructing body is a plug.

4. The device of claim 1, wherein the first obstructing body is a disc, and the second obstructing body is a disc.

5. The device of claim 1, wherein the first obstructing body is an expandable and collapsible basket and the second obstructing body is an expandable and collapsible basket.

6. The device of claim 1, further comprising a delivery member.

7. The device of claim 6, wherein the delivery member is a catheter.

8. The device of claim 1, wherein the reconstituted or naturally-derived collagenous material comprises an extracellular matrix (ECM) material.

9. The device of claim 8, wherein the ECM material is a submucosa.

10. The device of claim 8, wherein the ECM material is in a form of foam.

11. The device of claim 8, wherein the extracellular matrix (ECM) material comprises bioactive components native to a source tissue.

12. The device of claim 11, wherein the bioactive components comprise one or more growth factors.

13. The device of claim 12, wherein the growth factors are selected from the group consisting of basic fibroblast growth factor (FGF-2), transforming growth factor beta (TGF-beta), epidermal growth factor (EGF), and platelet derived growth factor (PDGF).

14. The device of claim 8, further comprising at least one of heparin, heparin sulfate, hyaluronic acid, and fibronectin.

15. The device of claim 1, wherein the reconstituted or naturally-derived collagenous material is in a fluidized form.

16. The device of claim 1, wherein the reconstituted or naturally-derived collagenous material is wrapped around the elongated member.

17. The device of claim 1, wherein the reconstituted or naturally-derived collagenous material is associated with the first obstructing body and the second obstructing body.

18. The device of claim 1, wherein the puncture or the opening is a vascular puncture made during a vascular, endoscopic, or orthopedic surgical procedures.

19. The device of claim 18, wherein the puncture or the opening is in a septum.

20. The device of claim 1, wherein the sealing material is associated with at least a portion or at least one element of the structural member by at least one of:
  i) lining an inner side of the first obstructing body;
  ii) lining an inner side of the second obstructing body; and/or
  iii) wrapping around the elongated member.

21. The device of claim 1, wherein the elongated member is one of a rod, a tube, a string, a thread, or a series of wires.

22. The device of claim 1, wherein the protruding structural elements are beads, tie-wrap-like elements, oriented fibers, or a combination thereof.

23. A method of using a medical device having (i) a structural member comprising an elongated member having a distal end and a proximal end, wherein at least a portion of the elongated member comprises protruding structural elements, a first obstructing body disposed on the distal end of the elongated member and having a first obstructing body perimeter enclosing a substantially solid surface; and a second obstructing body having a second obstructing body perimeter enclosing a substantially solid surface capable of being translated along the portion of the elongated member comprising the protruding structural elements for adjusting a distance between the first and the second obstructing bodies, wherein the first and the second obstructing bodies are configured to biodegrade or detach following the tissue ingrowth and the closure of the puncture or opening; and (ii) a remodelable sealing material associated with the structural member comprising reconstituted or naturally derived collagenous material for sealing a puncture or an opening through a wall of a blood vessel or a body cavity, wherein the sealing material is attached to or lining at least a portion of at least one of the elongated member, the first obstructing body and the second obstructing body, comprising the steps of
  deploying though a delivery member at the site of the puncture or opening the distal end of the elongated member on a luminal side of the blood vessel or body cavity so that the first obstructing body engages the inner surface of the wall of the blood vessel or body cavity at the puncture or the opening and at least the first obstructing body perimeter is in a continuous contact with the inner surface of the wall of the blood vessel or body cavity;
  deploying though a delivery member at site of puncture or the opening the proximal end of the elongated member on an outer side of the blood vessel or body cavity so that the second obstructing body is positioned on an outer surface of the wall of the blood vessel or body cavity at the puncture or the opening and at least the second obstructing body perimeter is in a continuous contact with the outer surface of the wall of the blood vessel or body cavity,
  wherein at least one of the first obstructing body and the second obstructing body radially expand so that the structural member assumes an expanded configuration following the deployment at the puncture or the opening to immediately seal the puncture or the opening and prevent leakage through the puncture or the opening,
  wherein the sealing material is substantially enclosed within the structural member once the structural member is in an expanded configuration and deployed at the site of the puncture or the opening and
  wherein the collagenous material encourages and promotes tissue ingrowth at the puncture or the opening.

24. The method of claim 23, wherein the puncture or the opening is a vascular puncture made during a vascular, endoscopic, or orthopedic surgical procedure.

25. The method of claim 23, wherein the puncture or the opening is in a septum.

26. The method of claim 23, wherein the second obstructing body is disposed on the proximal end of the elongated member after the proximal end of the elongated member is deployed.

27. A bodily opening closure system for immediate sealing of the bodily opening comprising:
  a) a structural member which can be in a first collapsed configuration and in a second expanded configuration, the structural member comprising:
    ii) a first obstructing body having a first obstructing body perimeter enclosing a substantially solid surface, the first obstructing body adapted to contact the interior of the bodily opening;
    ii) an elongated member fixed to the first obstructing body; and
    iii) a second obstructing body having a second obstructing body perimeter enclosing a substantially solid surface and disposed on the elongated member and capable of being translated along the elongated member;
  wherein the first obstructing body in the expanded configuration of the structural member has a diameter that is greater than the diameter of the elongated member, wherein at least a portion of the elongated member comprises protruding structural elements for adjusting a distance between the first and the second obstructing bodies, wherein the structural elements resist the travel back of the second obstructing body along the elongated member, and b) a remodelable sealing material associated with the structural member comprising a reconstituted or naturally-derived collagenous material wherein the collagenous material encourages and promotes tissue ingrowth, wherein the sealing material is attached to or lining at least a portion of at least one of the elongated member, the first obstructing body and the second obstructing body, wherein the sealing material is substantially enclosed within the structural member once the structural member is in an expanded configuration and deployed at the puncture or the opening;

wherein the first and the second obstructing bodies are opposing each other once the structural member is in the expanded configuration, wherein the first obstructing body is configured to be affixed against an inner surface of the wall of the bodily opening so that at least the first obstructing body perimeter is in a continuous contact with the inner surface of the wall of the bodily opening and the second obstructing body is configured to be affixed against an outer surface of the wall of the bodily opening so that at least the second obstructing body perimeter is in a continuous contact with the outer surface of the wall of the bodily opening once the structural member is placed at the bodily opening to immediately seal the bodily opening and prevent leakage through the opening; and wherein the first and the second obstructing bodies are configured to biodegrade or detach following the tissue ingrowth in the bodily opening.

28. The system of claim 27, wherein the reconstituted or naturally-derived collagenous material comprises an extracellular matrix (ECM) material.

29. The system of claim 28, wherein the ECM material is a submucosa.

30. The system of claim 28, wherein the ECM material is in a form of foam.

31. The system of claim 28, wherein the reconstituted or naturally-derived collagenous material comprises a folded or rolled sheet of ECM, with a central passage allowing the ECM to travel along the elongated member.

32. The system of claim 27, further comprising a delivery member having a body portion with a distal end, a proximal end, and a lumen extending between and through said ends, wherein the structural member in the collapsed configuration and the sealing material are disposed in the lumen of the delivery member.

33. The system of claim 27, wherein the protruding structural elements are beads, tie-wrap-like elements, oriented fibers, or a combination thereof.

34. The system of claim 27, wherein the first obstructing body has a convex exterior surface and an opposite open concave interior surface.

35. The system of claim 27, wherein the first obstructing body has a domed shape.

36. The system of claim 27, wherein the tissue ingrowth is at the bodily opening to close the opening.

37. The system of claim 27, wherein the first obstructing body has a cap shape.

38. The system of claim 37, wherein the second obstructing body has a disc shape.

39. A closure system for immediate sealing of a bodily opening, the device comprising:
  i) a first obstructing body having a first obstructing body perimeter enclosing a substantially solid surface, the first obstructing body in an expanded configuration of the device having a convex exterior surface, an opposite open concave interior surface, said first obstructing body adapted to contact the interior of the bodily opening and at least the first obstructing body perimeter is in a continuous contact with the interior surface of the wall of the bodily opening;
  ii) an elongated member fixed to the first obstructing body, wherein at least a portion of the elongated member comprises protruding structural elements; and
  iii) a remodelable sealing material attached to or lining at least a portion of at least one of the elongated member and the first obstructing body, the remodelable sealing material comprising a reconstituted or naturally-derived collagenous material, wherein the sealing material is substantially enclosed within the structural member once the structural member is in an expanded configuration and deployed at the bodily opening, and wherein the collagenous material encourages and promotes tissue ingrowth.

40. The device of claim 39, further comprising at least one disc associated with the elongated member, wherein the disc is capable of being translated along the elongated member.

41. The device of claim 40, wherein the protruding structural elements prevent the at least one disc from retracting backwards.

42. The device of claim 39, wherein the protruding structural elements are beads, tie-wrap-like elements, oriented fibers, or a combination thereof.

* * * * *